(12) United States Patent
Sewing et al.

(10) Patent No.: US 7,229,545 B2
(45) Date of Patent: Jun. 12, 2007

(54) PROCESS FOR THE COATING FOR METALLIC IMPLANT MATERIALS

(75) Inventors: Andreas Sewing, Dieburg (DE); Michel Dard, Seeheim-Jugenheim (FR); Sophie Roessler, Dresden (DE); Dieter Scharnweber, Dresden (DE); Hartmut Worch, Dresden (DE)

(73) Assignee: Biomet Deutschland GmbH, Berlin (DE)

( * ) Notice: Subject to any disclaimer, the term of this patent is extended or adjusted under 35 U.S.C. 154(b) by 0 days.

(21) Appl. No.: 10/414,284

(22) Filed: Apr. 16, 2003

(65) Prior Publication Data

US 2004/0033249 A1    Feb. 19, 2004

Related U.S. Application Data

(62) Division of application No. 09/885,287, filed on Jun. 21, 2001.

(30) Foreign Application Priority Data

Jun. 21, 2000    (DE) ................. 100 29 520

(51) Int. Cl.
    C25D 9/04    (2006.01)
    A61L 27/28    (2006.01)

(52) U.S. Cl. .............. 205/170; 205/188; 205/198; 205/199; 205/200; 205/316; 205/317; 205/318

(58) Field of Classification Search ........... 205/170, 205/188, 198, 199, 200, 316, 317, 318
See application file for complete search history.

(56) References Cited

U.S. PATENT DOCUMENTS

| | | | | |
|---|---|---|---|---|
| 4,214,952 | A | * | 7/1980 | Sato et al. ............... 205/148 |
| 4,713,076 | A | | 12/1987 | Draenert |
| 4,780,450 | A | | 10/1988 | Sauk et al. |
| 5,068,122 | A | | 11/1991 | Kokubo et al. |
| 5,205,921 | A | * | 4/1993 | Shirkanzadeh ........... 205/318 |
| 5,458,863 | A | * | 10/1995 | Klassen .................. 423/307 |
| 5,543,441 | A | | 8/1996 | Rhee et al. |
| 5,573,771 | A | | 11/1996 | Geistlich et al. |
| 5,578,188 | A | * | 11/1996 | Mertens et al. .......... 205/334 |
| 5,723,038 | A | * | 3/1998 | Scharnweber et al. .... 205/107 |
| 6,113,993 | A | * | 9/2000 | Gao et al. ............... 427/573 |
| 6,376,573 | B1 | * | 4/2002 | White et al. ............. 523/115 |

(Continued)

FOREIGN PATENT DOCUMENTS

DE        34 09 372        9/1985

(Continued)

OTHER PUBLICATIONS

European International Search Report issued Dec. 5, 2001 in EP 01 11 2667.

(Continued)

*Primary Examiner*—Roy King
*Assistant Examiner*—William T. Leader
(74) *Attorney, Agent, or Firm*—Millen, White, Zelano, Branigan, P.C.

(57) ABSTRACT

A biomimetically produced bone-analogous coating, comprising organic and inorganic main constituents, is suitable for coating metallic implant materials of any desired surfaces. The coating comprises a collagen matrix mineralized with calcium phosphate.

33 Claims, 1 Drawing Sheet

U.S. PATENT DOCUMENTS

| | | | |
|---|---|---|---|
| 6,384,195 B1 | 5/2002 | Delgado et al. | |
| 6,384,197 B1 | 5/2002 | Weis et al. | |
| 6,428,978 B1 * | 8/2002 | Olsen et al. | 435/69.1 |
| 6,506,217 B1 * | 1/2003 | Arnett | 623/23.61 |
| 6,524,718 B1 * | 2/2003 | Worch et al. | 428/472 |

FOREIGN PATENT DOCUMENTS

| | | |
|---|---|---|
| DE | 3414924 | 10/1985 |
| DE | 19504386 | 8/1996 |
| DE | 196 43 5555 | 4/1998 |
| DE | 198 11 900 | 9/1999 |
| DE | 198 12 713 | 9/1999 |
| DE | 198 12 714 | 9/1999 |
| DE | 19811900 | 9/1999 |
| EP | 0 389 713 | 10/1990 |
| WO | WO 92/13984 | 8/1992 |
| WO | WO 9213984 | 8/1992 |
| WO | WO 98/17844 * | 4/1998 |
| WO | WO 99/30672 | 6/1999 |

OTHER PUBLICATIONS

L. Floquet et al., "Le comportement biologique in vitro d'un alliage TiNb30 traité avec hydroxyapatite . . ." Rev. Stomatol. Chir. Maxillofac., (1997), 98, Sup. 1, pp. 47-49.

M.J. Filiaggi, et al., "Post-plasma-spraying heat treatment of the HA coating/Ti-6A1-4V implant system", Journal of Biomedial Materials Res., (1993), vol. 27, pp. 191-198.

K.A. Gross, "In Vitro Changes of Hydroxyapatite Coatings", The Intenrational Journal of Oral & Maxilofacial Implants, pp. 589-597.

M. Shirkhanzadeh, "Direct formation of nanophase hydroxyapatite on cathodically polarized electrodes", Journal of Materials Science: Materials in Medicine 9, (1998), pp. 67-72.

C.Y.Yang, "Bond degradation at the plasma-sprayed HA coating/Ti-6A1-4V alloy interface: an in vitro study", Journal of Materials Science: Materials in Medicine 6, (1995), pp. 258-265.

P. Schaffner, et al., "inducted tissue integration of bone implants by coating with bone selective RGD-peptides", Journal of Materials Science: Materials in Medicine, 10, (1999), pp. 837-839.

P. Remer, "Schwerpunktprogramm Gradientenwerkstoff", (1998), pp. 2-45, w/translation of relevant parts of non-English documents.

A. S. Posner, et al., "Chapter 11 Chemistry and Structure of Precipitated Hydroxyapatites" The Hospital for Special Surgery Cornell Univ. Med. Coll., pp. 330-350., date not available.

Szmukler-Moncler Serge, et al., "Evaluation of a soluble calcium phosphate coating obtained by electrochemical deposition. . . ." pp. 481-485, date not available.

"Standard Specification for Wrought Titanium 6A 1-4V.ELI Alloy for Surgical Implant Application", pp. 17-19., date not available.

\* cited by examiner

PROCESS FOR THE COATING FOR METALLIC IMPLANT MATERIALS

This application is a division of U.S. application Ser. No. 09/885,287, filed Jun. 21, 2001.

The invention relates to a biomimetically produced bone-analogous coating, comprising an organic and inorganic main constituent, for metallic implant materials of any desired surface geometry and to a process for its preparation. The main components of this coating are collagen and calcium phosphate phases which form the organic and inorganic main constituent of the bone. The coating according to the invention is suitable to a particular extent as a matrix for the inclusion of further inductive substances such as growth factors, adhesion proteins or pharmacological active compounds.

On the question of an improved adaptation of the physicochemical and biochemical properties of the surfaces of implants to the local surrounding tissue with the aim of optimizing the biocompatibility and biofunctionality, various approaches have been followed.

In addition to mere changes in the topography of the implant surface, such as etching or sand blasting, at present coatings with calcium phosphate phases (CPP) play an important role. Most widely advanced in use is the coating of implants in contact with bone with hydroxyapatite and increasingly also more readily soluble calcium phosphate phases [Yang et al., J. Mater. Sci., Mater. in Med. 6, 258–65 (1995); Remer, P., Schwerpunktprogramm Gradientenwerkstoffe, 3rd Ed. Darmstadt 31.3.1998; Floquet et al., Rev. Stomatol. Chir. Maxillofac. 98, 47–9 (1997)]. These methods for the coating of implants with the inorganic main component of bone and compounds derived therefrom aim particularly at a more rapid establishment of the implant due to a locally increased supply of calcium and phosphate ions. The coating of implant surfaces with calcium phosphate phases—(CPP) is at present mainly carried out by plasma spraying processes. On account of the process conditions, these layers have properties which differ strongly in crystallinity and solution behaviour from the mineral phase of the bone and on account of the high layer thicknesses can lead to the mechanical failure of the layers [Filiaggi et al., J. Biomed. Mat. Res. 27(2), 191–8 (1993); Gross et al., Int. J. Oral Maxillofac. Implants 12 (5), 589–97 (1997); Posner et al., Phosphate Minerals, Springer Verlag, Berlin/Heidelberg (1984)].

Electrochemically assisted processes [Shirkhanzadeh, J. Mater. Sci.:Mater. in Med. 9, 76–72 (1998); Szmukler-Moncler et al., Biological Mech. Of Tooth Eruption, Resorption and Replacement by implants (Eds. Z. Davidovitch and J. Mah), 481–85 Harvard Society for the Advancement of Orthodontics, Boston, USA (1998)] offer the possibility of producing calcium phosphate phases (CPP) with lower layer thicknesses. The deposition of calcium phosphate phases (CPP) is realized by cathodic polarization of the implant in $Ca^{2+}/H_xPO_4^{(3-x)-}$-containing solution. The polarization of the implant leads to an alkalization of the electrolyte near to the surface ($2H_2O+2e^-\rightarrow H_2+2OH^-$), by means of which a precipitation reaction is induced in front of the sample surface and the precipitation product formed is deposited on the metallic implant surface.

A further approach to the field of surface modification of implant materials consists in achieving a 'biologization' of implant surfaces by utilizing organic compounds occurring in surrounding tissue for the surface modification. In this connection, on the one hand, immobilized proteins and protein sequences are used which exert their action in the immobilized state (collagen, adhesion proteins, RGD sequences) or proteins which are released over a certain period of time. Depending on the immobilized substance, a largely general, positive action on the biocompatibility of the implant surface (collagen, certain adhesion proteins) or the adhesion of certain cell types is aimed at (extended RGD sequences) [Schaffner et al., J. of Mat. Sci.: Mat. in Med. 10, 837–39 (1999)].

The prior art previously mentioned shows that processes which have set themselves the goal of the production of a bone-analogous composite phase, formed from the inorganic and organic constituents of the bone for the coating of metallic implants were unknown up to now. Methods which comprise both hydroxyapatite and collagen are only restricted to mixtures of the components which are moreover assigned to further exogenous substances as carrier materials.

WO 99/30672 (Uni Tübingen) describes a coating for prostheses of organic polymer material in whose surface hydroxyapatite or collagen can be included. The polymer material here is only the adhesion promoter; a composite of collagen and a calcium phosphate phase which is similar to bone cannot be referred to.

A further possibility for the inclusion of scleroproteins and calcium phosphate is presented in DE19811900 (Feinchemie). A biocompatible composite material consisting of an inorganic gel and a bioactive component (collagen, elastin, fibrin) is described. Moreover, calcium phosphates or their precursors can be present in the dissolved form. This composite material is accordingly only a mixture of the main constituents of the bone, which is moreover assigned to an inorganic gel as a carrier.

In WO 92/13984 (Queen's University of Kingston), a process for the electrochemical production of ceramic coatings from calcium phosphate compounds is described. It is not excluded here that the electrolyte also contains biological non-toxic compounds such as collagen or impurities. The coating is a uniform microporous ceramic material made of associated non-orientated crystallites. This layer can also contain biologically active compounds as precipitation products. As a ceramic calcium phosphate coating, the coating described accordingly differs markedly from a mineralized collagen/calcium phosphate matrix.

Implants for use in the maxillary area or joint replacement are preferably manufactured from metallic materials in order to meet the mechanical demands. Here, the immediate surface, which can differ greatly from the basic material in its properties, is often neglected. However, it is known that the properties of the surface especially are of crucial importance for the interactions between implant and surrounding tissue. Thus conformational changes of adsorbed proteins can contribute significantly to formation of a fibrous intermediate layer, which in turn can result in an inadequate stability of the implant.

SUMMARY OF THE INVENTION

A teaching of the present invention starts from the object of modifying implant surfaces specifically with biochemical information in order to achieve a rapid osteointegration with formation of high-grade bony tissue after implantation.

Upon further study of the specification and appended claims, further objects and advantages of this invention will become apparent to those skilled in the art.

The objects are achieved by means of a bone-analogous coating, comprising organic and inorganic main constituents, for implant materials of any desired surface geometry, the coating comprising a collagen matrix mineralized with calcium phosphate.

Suitable implant materials are generally conductive materials such as conductive polymers or metals used in dental technology or in the endoprosthesis and trauma fields. Titanium and titanium alloys such as $TiAl_6V_4$ are particularly preferred.

The coating according to the invention is produced under conditions which make possible the inclusion of organic components. For the biomimetic production of a matrix which is analogous to bone, the invention therefore utilizes electrochemically assisted processes, which can be carried out under almost physiological pH and temperature conditions and thus make possible the inclusion of biomolecules. These can be present in the electrolyte solution or in immobilized form on the implant surface. The main components of the layer consist of collagen and hydroxyapatite, the organic and inorganic main component of the bone. By means of the subject according to the invention, it is possible for the first time to comprehend a permeable structure, analogous to the bone structure produced in vivo, in its essential features in vitro and to produce it with good adhesion to a metallic implant surface.

The mineralised collagen matrix is constructed in the form of layers. This has the advantage that by means of this the production of graded layers having a varying degree of mineralization of the collagen matrix is also possible. The preferred overall thickness of the matrix coating is about 0.04 μm–150 μm, especially about 3–8 μm. The preferred range for the typical dimensions of the hydroxyapatite crystals is about 300–500 nm in length and 50–60 nm in diameter.

The inorganic main constituent or the calcium phosphate phase (CPP) preferably contain amorphous calcium phosphate $(Ca_9(PO_4)_6.nH_2O)$, hydroxyapatite $(Ca_{10}(PO_4)_6(OH)_2)$, octacalcium phosphate $(Ca_8H_2(PO_4)_6.H_2O)$ or brushite $(CaHPO_4.2H_2O)$. However, mixtures of the phases mentioned beforehand are also possible.

The calcium phosphate phase can additionally be doped with ions such as fluoride, silver, magnesium or carbonate.

The use of type I collagen is preferred, which is responsible in the bone for the elastic properties and in the mineralized state brings about the high strength of the bone together with the hydroxyapatite crystallites. Furthermore, the collagen can also be a mixture of the types I to III. The types I to III belong to the group of fibril-forming collagens. Gelatin can additionally be added to the collagen. In addition to collagen, which can also be derived from recombinant production, the, inclusion of other matrix proteins is also possible.

A further advantage of the invention involves the possibility of utilizing the layers described as a matrix for bone-specific proteins (BMP, TGFβ etc.). In addition to growth factors and cell-specific adhesion peptides, the inclusion of pharmacological active compounds, such as antibiotics, is also possible.

The invention further relates to a metallic implant made of a parent substance and of an outer layer carried by this, the outer layer being a coating according to the invention.

The invention also relates to a process for the electrochemically assisted coating of metallic implant materials of any desired surface with collagen and calcium phosphate phases (CPP), comprising a) coating of the metallic implant material by immersion in a collagen solution at a pH of about less than 8 and a temperature of about 4 to 40° C. for a few minutes.

b) coating of the collagen-coated sample with calcium phosphate phases (CPP) in an electrochemically assisted process by means of galvanostatic polarization in an electrolyte solution comprising calcium ions and phosphate ions under defined current density and temperature. The preferred ranges for current density and temperature are, respectively about −0.2 to −50 mA/cm$^2$ and about 30–40° C., more preferably a current density of about −1 to −10 mA/cm$^2$ and a temperature of about 37° C.

The above process steps a and b may be preformed simultaneously or sequentially.

The coating can be carried out in an electrolysis cell in which the metallic implant is cathodically polarized. The layer deposition takes place near to physiological pH and temperature conditions. The electrolyte comprises a $Ca^{2+}/H_xPO_4^{(3-x)-}$-containing solution, which can additionally contain collagen or other substances (growth factors, antibiotics). The implant surface can have any desired surface geometry (structure; rough, polished, etched), a chemical modification (generation of functional groups), a calcium phosphate layer, a protein layer and a layer prepared according to Patent No. WO 98/17844 (TU Dresden) or DE-19504386 (TU Dresden) or a combination thereof. By means of a process of calcium phosphate deposition and the immobilization of collagen under physiological pH and temperature conditions, which is carried out simultaneously, a mineralized collagen layer can be produced on the titanium surface. The degree of the mineralization, i.e. the nature of the calcium phosphate phases (CPP) and degree of coating, are specified here by the electrochemical parameters. This process can be assisted by the addition of groups of substances influencing mineralization (e.g. bone sialoprotein, osteopontin).

Preferably, the coating process comprises firstly carrying out a coating of the sample with calcium phosphate phases (CPP) in an electrochemical process via galvanostatic polarization in an electrolyte solution comprising calcium ions and phosphate ions at defined current density and temperature, followed by a coating of the sample, coated with calcium phosphate phases (CPP), by immersion in a collagen solution at a pH of less than 8 and a temperature of about 4 to 40° C. for a few minutes, and subsequently coating of the collagen/CPP-coated sample with further calcium phosphate phases (CPP) in a fresh electrochemical process by means of galvanostatic polarization under defined current density and temperature.

The process steps mentioned beforehand can preferably also proceed a number of times under alternating conditions, i.e. a sequence of the process steps a) and b) according to the scheme a-b-a-b-a-b etc.

Also preferred is a process in which the process steps a) and b) are combined into one step, the metallic implant material to be coated being electrochemically polarized cathodically in a collagen solution comprising calcium ions and phosphate ions.

A process is even more preferred in which a cathodic current flow of −0.5 to −30 mA/cm$^2$ flows for approximately 30 minutes during the galvanostatic polarization in process step b).

The advantages of the mineralised bone-analogous collagen matrix according to the invention can be shown impressively in the cell test. While cell adhesion for osteoblasts still shows comparatively good values with biomimetically produced hydroxyapatite layers after one hour, cell proliferation on the layers according to the invention is clearly preferred. The increase in the cell count takes place here at a significantly earlier point in time and the maximum value of the cell count is very much more rapidly achieved than for pure hydroxyapatite layers. A corresponding measurement curve for a proliferation test over the course of 17 days with MC3T3 mouse osteoblasts is shown in FIG. 1.

The invention is described and explained in greater detail below with the aid of exemplary embodiments with reference to FIG. 1.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German Application No. 100 29 520.7, filed Jun. 21, 2000 is hereby incorporated by reference.

EXAMPLE 1

A cylinder of $TiAl_6V_4$ (h=2 mm, Ø 10 mm) is metallographically prepared using a sealing $TiO_2$ polish. The cylinder is then cleaned in acetone and ethanol in an ultrasonic bath and rinsed with distilled water.

The sample is then immersed in a collagen solution which is prepared in the following manner: acid-soluble freeze-dried calf skin collagen type I is dissolved in 0.01 M acetic acid and adjusted to a concentration of 0.1 mg/ml at 4° C. The collagen molecules are reconstituted in two process steps: pH adjustment to 7.4 using double-concentrated phosphate buffer and temperature increase to 36° C. After 3 hours, the solution consists of native reconstituted fibrils. The sample remains in this solution for 10 minutes, then it is rinsed with deionized water.

The sample coated with collagen is incorporated as a working electrode in a three-electrode arrangement, consisting of a saturated calomel electrode as reference electrode and a platinum sheet as counter-electrode in a thermostated electrolysis cell. The electrolyte solution used is a stock solution which is prepared in the following way: 10 ml of stock solution of $CaCl_2$ and $NH_4H_2PO_4$ in each case, in the concentrations 33 mM and 20 mM, are diluted and mixed so that 200 ml result; 1.67 mM in calcium ions and 1.0 mM in phosphate ions. The pH is adjusted to 6.4 using dilute $NH_4OH$ solution.

After connection to the potentiostat, mineralization/coating with calcium phosphate phases (CPP) is carried out by means of galvanostatic polarization under cathodic current flow at $-1$ mA/cm$^2$. After 30 minutes, the cathodic polarization is complete; the sample is taken out of the electrolyte solution and rinsed with deionized water. The deposited layer appears whitish. Electron-microscopic examination shows a layer consisting of a collagen network and spherical CP clusters. IR-spectroscopic investigations furnish proof that the mineral phase consists of amorphous calcium phosphate.

EXAMPLE 2

A cylinder of $TiAl_6V_4$ is prepared as in Example 1. The construction of the electrolysis cell and the electrolyte for calcium phosphate deposition are identical to that in Example 1.

After connection to the potentiostat, coating with CPP is carried out by means of galvanostatic polarization under cathodic current flow at $-10$ mA/cm$^2$. After 30 minutes, the cathodic polarization is interrupted, and the sample is taken out of the electrolyte solution and rinsed with deionized water. A crystalline CPP, hydroxyapatite, is now present on the $TiAl_6V_4$ surface. The sample is now immersed in a collagen solution which is identical to that in Example 1. The sample coated with hydroxyapatite remains in this solution for 10 minutes, then it is rinsed with deionized water and again incorporated into the electrolysis cell. After connection to the potentiostat, deposition of hydroxyapatite again takes place by means of galvanostatic polarization under cathodic current flow at $-10$ mA/cm$^2$. After 20 min, the sample is taken out and rinsed with deionized water. The deposited layer appears whitish. Electron-microscopic examination shows a closed layer which consists of agglomerates of small needles. A network of mineralized collagen fibrils is situated on this layer. IR-spectroscopic and X-ray diffraction investigations furnish proof that the mineral phase consists of hydroxyapatite. The characteristic amide bands in the IR spectrum furthermore show that the collagen is not present in denatured form, but on the contrary a good agreement exists between the mineralized layer and a spectrum for native bone.

EXAMPLE 3

A cylinder of $TiAl_6V_4$ is prepared as in Example 1. The construction of the electrolysis cell is identical to that in Example 1.

A collagen solution containing native assembled collagen fibrils is prepared as in Example 1. This solution is centrifuged at 5000 g and 4° C. for 15 min, and the pellet is taken up with deionized water and dispersed by shaking. The solution is then centrifuged at 5000 g and 4° C. again for 15 min. The pellet obtained in the centrifugation is now taken up in the electrolyte for calcium phosphate deposition described in Example 1 and homogenized by means of a disperser.

This solution is used as an electrolyte for a simultaneously carried-out process for the deposition and mineralization of collagen. After connection to the potentiostat, mineralization is carried out by means of galvanostatic polarization under cathodic current flow at $-10$ mA/cm$^2$. After 30 minutes, the cathodic polarization is complete, and the sample is taken out of the electrolyte solution and rinsed with deionized water.

The deposited layer appears whitish. Electron-microscopic examination shows a composite of collagen fibrils and CPP. IR-spectroscopic and X-ray diffraction investigations furnish proof that the mineralization of the fibrils takes place mainly by means of the crystalline phase hydroxyapatite. The more readily soluble amorphous calcium phosphate phase is partially found. The characteristic amide bands in the IR spectrum furthermore show that the collagen is not present in denatured form, but on the contrary a good agreement exists between the mineralized layer and a spectrum for native bone.

EXAMPLE 4

A cylinder of $TiAl_6V_4$ is prepared as in Example 1. The construction of the electrolysis cell and the electrolyte for the calcium phosphate deposition are identical to that in Example 1.

After connection to the potentiostat, coating with CPP by means of galvanostatic polarization is carried out under cathodic current flow at $-10$ mA/cm$^2$. After 30 minutes, cathodic polarization is interrupted, and the sample is taken out of the electrolyte solution and rinsed with deionized water. A crystalline CPP, hydroxyapatite, is now present on the $TiAl_6V_4$ surface. The sample is now immersed in a collagen solution which is identical to that in Example 1. The sample coated with hydroxyapatite remains in this solution for 10 minutes, then it is rinsed with deionized water and again incorporated into the electrolysis cell. After connection to the potentiostat, partial mineralization of the collagen is carried out under cathodic current flow at $-10$ $mA/cm^2$ for 15 min. Finally, the sample is rinsed with deionized water. The deposited layer appears whitish. In a second process step, the binding of integrin-specific cell-selective peptide sequences to the immobilized collagen layer is carried out. The binding is carried out covalently by means of a thiol anchor and SMPB (sulfosuccinimidyl 4-(p-maleimidophenyl)butyrate) to the phosphate groups of the collagen.

Electron-microscopic examination shows a homogeneous layer of hydroxyapatite needles, on which a partially mineralized network of collagen fibrils is present. The activity of the RGD sequences is evident from adhesion and proliferation experiments using MC3T3-E1 cells. Relative to comparable pure collagen layers, the RGD-coated surfaces show increased cell adherence and cell proliferation beginning after shorter times.

BRIEF DESCRIPTION OF THE DRAWINGS

Various other features and attendant advantages of the present invention will be more fully appreciated as the same becomes better understood when considered in conjunction with the accompanying drawings, in which like reference characters designate the same or similar parts throughout the several views, and wherein:

FIG. 1 shows the cell proliferation of MC3T3 mouse osteoblasts on hydroxyapatite and on the bone-analogous collagen/hydroxyapatite matrix, in each case on $TiAl_6V_4$ substrates. The absorption is proportional to the cell count (WST-1 test).

Figure 1:
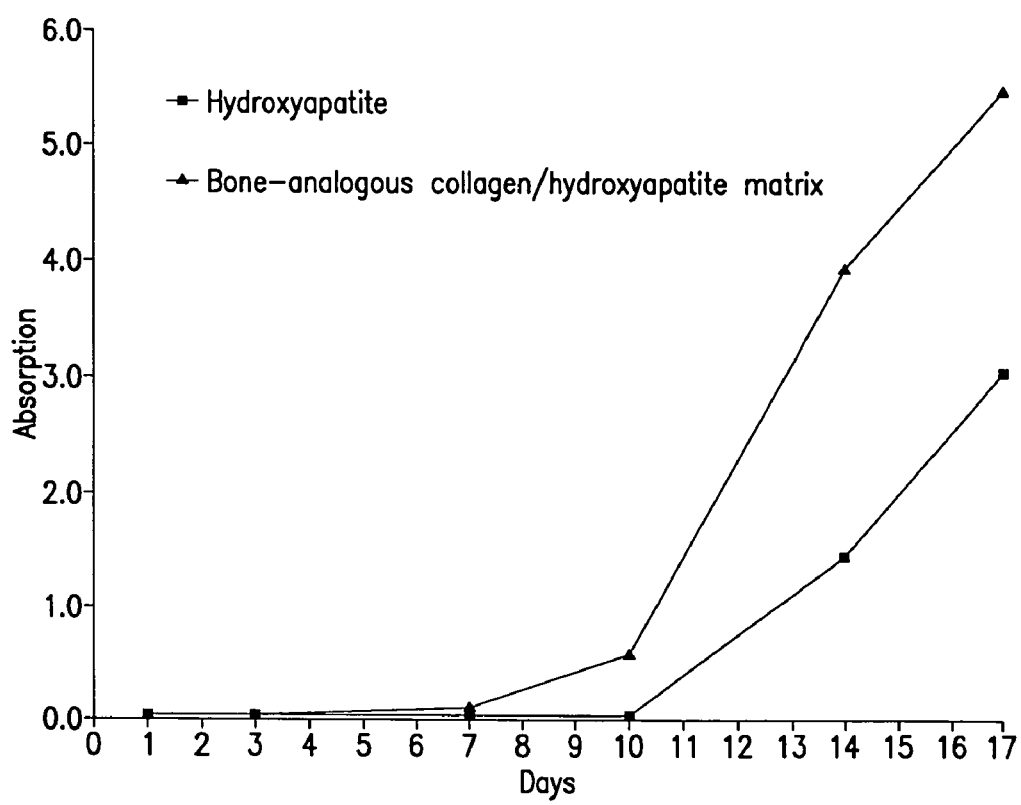

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for the electrochemical coating of metallic implant materials with a mineralized collagen matrix comprising:
   a) coating a metallic implant material by immersion in a collagen solution at a pH of less than 8 and a temperature 4–40° C., and
   b) coating said metallic implant material with a calcium phosphate phase (CPP) in an electrochemically assisted process by means of galvanostatic polarization in an electrolyte solution comprising calcium ions and phosphate ions, wherein process steps a) and b) are performed sequentially.

2. A process according to claim 1, wherein an additional process step b) is placed in front of process step a).

3. A process according to claim 1, wherein the process step a) and b) proceed alternatively a number of times.

4. A process according to claim 1, wherein the process steps a) and b) are combined into one step, the metallic implant material to be coated being electrochemically polarized cathodically in a collagen solution comprising calcium ions and phosphate ions.

5. A process according to claim 1, wherein a cathodic current flow of $-02$ to $-50$ $mA/cm^2$ flows for 25 to 40 minutes during the galvanostatic polarization in process step b).

6. A process according to claim 1, wherein the mineralized collagen matrix is layered.

7. A process according to claim 1, wherein the coating further comprises gelatin.

8. A process according to claim 1, wherein a cathodic current flow of $-0.5$ to $-30$ $mA/cm^2$ flows for 30 to 40 minutes during the galvanostatic polarization in process step b).

9. A process according to claim 1, wherein a cathodic current flow of $-1$ to $-10$ $mA/cm^2$ flows during the galvanostatic polarization in process step b).

10. A process according to claim 1, wherein the galvanostatic polarization in process step b) is performed at a temperature of 30–40° C.

11. A process according to claim 1, wherein the pH of process step a) is between about 7.4 and 8.

12. A process according to claim 1, wherein the calcium phosphate phase contains amorphous calcium phosphate $(Ca_9(PO_4)_6.nH_2O)$, hydroxyapatite $(Ca_{10}(PO_4)_6(OH)_2)$, octacalcium phosphate $(Ca_8H_2(PO_4)_6.5H_2O)$, brushite $(CaHPO_4.2H_2O)$ or mixtures thereof.

13. A process according to claim 1, wherein the calcium phosphate phase is doped with fluoride, silver, magnesium or carbonate ions or combinations thereof.

14. A process according to claim 1, wherein the collagen is collagen of type I.

15. A process according to claim 1, wherein the collagen is a mixture of collagen of types I to III.

16. A process according to claim 1, further containing growth factors, peptide sequences, hormones, antibiotics or mixtures thereof.

17. A process according to claim 1, wherein the metallic implant is made of titanium or titanium alloy.

18. A process for the electrochemical coating of metallic implant materials with a mineralized collagen matrix comprising coating a metallic implant material by immersion in a homogenized electrolyte solution comprising calcium ions, phosphate ions, and collagen at a pH of less than 8 and a temperature 4–40° C. in an electrochemically assisted simultaneously carried-out process by means of galvanostatic polarization, whereby the electrolyte solution is prepared in a process comprising:
   a) preparing a collagen solution in a two step process by dissolving collagen in an acid followed by adjusting the pH to 7.4 using a phosphate buffer and increasing the temperature,
   b) after 3 hours centrifuging the solution,
   c) dissolving the resultant collagen pellet in a solution comprising calcium and phosphate ions, and
   d) homogenizing the resulting electrolyte solution in a disperser.

19. A process according to claim 18, wherein a cathodic current flow of $-02$ to $-50$ $mA/cm^2$ flows for 25 to 40 minutes during the galvanostatic polarization.

20. A process according to claim 18, wherein the mineralized collagen matrix is layered.

21. A process according to claim 18, wherein the coating further comprises gelatin.

22. A process according to claim 18, wherein a cathodic current flow of −0.5 to −30 mA/cm$^2$ flows for 30 to 40 minutes during the galvanostatic polarization.

23. A process according to claim 18, wherein a cathodic current flow of −1 to −10 mA/cm$^2$ flows during the galvanostatic polarization.

24. A process according to claim 18, wherein the galvanostatic polarization is performed at a temperature of 30–40° C.

25. A process according to claim 18, wherein the pH is between about 7.4 and 8.

26. A process according to claim 18, wherein the solution comprising calcium and phosphate ions contains amorphous calcium phosphate ($Ca_9(PO_4)_6 \cdot nH_2O$), hydroxyapatite ($Ca_{10}(PO_4)_6(OH)_2$), octacalcium phosphate ($Ca_8H_2(PO_4)_6 \cdot 5H_2O$), brushite ($CaHPO_4 \cdot 2H_2O$) or mixtures thereof.

27. A process according to claim 18, wherein the solution comprising calcium and phosphate ions is doped with fluoride, silver, magnesium or carbonate ions or combinations thereof.

28. A process according to claim 18, wherein the collagen is collagen of type I.

29. A process according to claim 18, wherein the collagen is a mixture of collagen of types I to III.

30. A process according to claim 18, further containing growth factors, peptide sequences, hormones, antibiotics or mixtures thereof.

31. A process according to claim 18, wherein the metallic implant is made of titanium or titanium alloy.

32. A process for the electrochemical coating of metallic implant materials with a mineralized collagen matrix comprising:
 a) coating a metallic implant material by immersion in a collagen solution at a pH of less than 8 and a temperature 4–40° C., and
 b) coating said metallic implant material with a calcium phosphate phase (CPP) in an electrochemically-assisted process by means of galvanostatic polarization in an electrolyte solution comprising calcium ions and phosphate ions, wherein process steps a) and b) are performed simultaneously or sequentially and wherein an additional process step b) is placed in front of process step a).

33. A process for the electrochemical coating of metallic implant materials with a mineralized collagen matrix comprising:
 a) coating a metallic implant material by immersion in a collagen solution at a pH of less than 8 and a temperature 4–40° C., and
 b) coating said metallic implant material with a calcium phosphate phase (CPP) in an electrochemically-assisted process by means of galvanostatic polarization in an electrolyte solution comprising calcium ions and phosphate ions, wherein process steps a) and b) are performed simultaneously or sequentially and wherein the process step a) and b) proceed alternatively a number of times.

* * * * *